United States Patent [19]

Dvorsk et al.

[11] Patent Number: 4,758,671

[45] Date of Patent: Jul. 19, 1988

[54] WATER-SOLUBLE CATION-ACTIVE POLYELECTROLYTES

[75] Inventors: Drahomír Dvorský; Karel Čeřovský; Jirí Lukáč, all of Dvůr Králové nad Labem; Jaromír Socha, Pardubice, all of Czechoslovakia

[73] Assignee: Vyzkumny ustav textilniho zuslechtovani, Dvur Králové nad Labem, Czechoslovakia

[21] Appl. No.: 3,111

[22] Filed: Jan. 14, 1987

Related U.S. Application Data

[63] Continuation-in-part of Ser. No. 738,595, May 28, 1985, abandoned.

[30] Foreign Application Priority Data

May 28, 1984 [CS] Czechoslovakia .................. 3987-84
Jun. 7, 1984 [CS] Czechoslovakia .................. 4316-84

[51] Int. Cl.$^4$ .................. C07D 233/60; C09B 67/10
[52] U.S. Cl. .................. 548/341; 8/573; 548/354
[58] Field of Search .................. 548/341, 354

[56] References Cited

U.S. PATENT DOCUMENTS

| | | | |
|---|---|---|---|
| 4,366,036 | 12/1982 | Lash et al. | 548/341 |
| 4,499,282 | 2/1985 | Dvorsky et al. | 548/336 |
| 4,613,609 | 9/1986 | Diamond et al. | 548/341 |
| 4,692,450 | 9/1987 | Cassal et al. | 548/341 |

Primary Examiner—Richard A. Schwartz
Assistant Examiner—J. Richter
Attorney, Agent, or Firm—Klein and Vibber

[57] ABSTRACT

The present invention relates to a water-soluble cation-active polyelectrolyte which can be prepared by reacting one mole of a compound having the formula $$[R_1-A-B(-R_2)_x]^{m+}m/r\ X^{r-}$$

wherein
  X is anionic residue of a strong inorganic or organic acid;
  r is an integer of 1, 2, or 3;
  x is an integer of 1 or 2;
  A is $-CH_2-CH(OH)-CH_2-M^+-CH_2-CH(OH)-CH_2-$,
  M is a bifunctional heterocyclic imidazole residue,
  B is selected from the group consisting of $-[N-R_3-(CH_2)_n]_s-NR_4-$ and $-[NR_4-(CH_2)_n]_s-NR_3-$ when x=1 and
  $=[N-(CH_2)_n]_s-NR_4-$, $-[NR_3-(CH_2)_n]_s-N=$, $=[N-(CH_2)_n-NR_3]_s-$, and $-[NR_4-(CH_2)_n-N]_s=$, when x=2,
  $R_1$ is selected from the group consisting of Cl—, —OH, and H—B—,
  $R_2$ is selected from the group consiting of H, —A—Cl, —A—OH, —A—B—H, and —A—B—A—$R_1$,
  $R_3$ and $R_4$ are each selected from the group consisting of a hydrogen or an alkyl group having 1–4 carbon atoms,
  n is an integer of from 2 to 10, and
  s is an integer of from 1 to 4.

These compounds can be used in textile finishing technology to improve the fastness of dyes. The polyelectrolytes of the invention improve the ability of cellulose fibers to accept and retain dyes, thus increasing the fastness or reactive dyes. In particular, the invention represents an improvement over known methods of washing cellulose fibers after dyeing.

2 Claims, No Drawings

WATER-SOLUBLE CATION-ACTIVE POLYELECTROLYTES

This application is a continuation-in-part of application Ser. No. 738,595, filed May 28, 1985 now abandoned.

The invention relates to water-soluble cation-active polyelectrolytes useful in textile finishing. The polyelectrolytes of the invention improve the ability of cellulose fibers to accept and retain dyes; thus increasing the dye fastness of reactive dyes. In particular, the invention represents an improvement over known methods of washing cellulose fibers after dyeing.

BACKGROUND OF THE INVENTION

Textile finishing agents that improve the dyeability of cellulose fabrics are known. Among these are quaternary ammonium compounds derived from tertiary amines and epichlohydrin, and having the reactive group

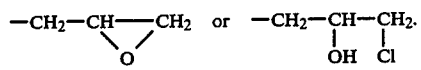

Dvorsky et al., U.S. Pat. No. 4,499,282.

These known compounds are characterized by the formula

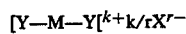    FORMULA Ia, or by the formula

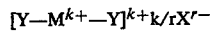    FORMULA Ib, where Y is a reactive group as defined above, r is an integer of 1–3; k is an integer of 1 or 2; X is an anionic residue of a strong inorganic or organic acid; and M is a residue derived from a heterocycle with two nitrogen atoms. (These formulas for the quaternary ammonium compounds are the same, except that Formula Ib shows the location of the k+ charge.) The compounds of Formula I are used to finish cellulose fibers; they greatly improve the dye fastness of substantive dyes, and also somewhat improve the fastness of anionic and other reactive dyes.

After dyeing it is necessary to remove excess dye and ancillary chemicals by washing, a time-consuming process that requires large amounts of water and energy. With some dyes it is necessary to increase the fastness of the dye to prevent subsequent bleeding. One method of improving fastness is to create a complex between the dye molecule and a macromolecular compound having an opposite charge.

Washing and fastness are particularly important and complex when dyeing and printing cellulose fibers with reactive dyes. When a reactive dye is used to color a cellulose fabric, only one active site reacts with the fiber. A relatively large portion of each dye molecule hydrolyzes and must be removed. Dye and print fastness therefore depends to a large degree on the efficiency of the washing process: the more hydrolyzed dye that is removed, the better the washing process.

Many solutions have been sought with regard to the problems of dyeing and washing when reactive dyes are used. With regard to the dying compounds themselves, specific dyes and dyeing conditions have been sought which maximize the binding of dye molecules to the fabric fibers, and thus minimize the amount of excess hydrolyzed dye to be removed by washing. Another solution would be to select bifunctional dye molecules and achieve dyeing conditions which promote the removal of the excess hydrolyzed portion after dyeing. In such a scheme, the active portion of the dye molecule binds firmly to the fibers, while the excess portion is bound less firmly to the active portion and is easily released during washing.

Various washing technologies are also known. One method relies on the use of a suspension of solid sorbents. This method, however, is expensive and relatively inefficient. Another method relies on cationic agents applied after washing. The purpose of the agent is to block the dye residues which remain after washing. This method, as heretofore known, has suffered from a serious disadvantage: the fastness of the dye when exposed to light is impaired.

SUMMARY OF THE INVENTION

It is an object of the present invention to provide an improved method of removing the excess hydrolyzed portion of reactive dyes from cellulose fibers after dyeing. It is another object of the invention to improve dye fastness when other anionic dyes, particularly direct dyes, are used.

The invention provides a finishing agent, and a method for its use, comprising a series of cation-active polyelectrolytes having a structural group of the formula

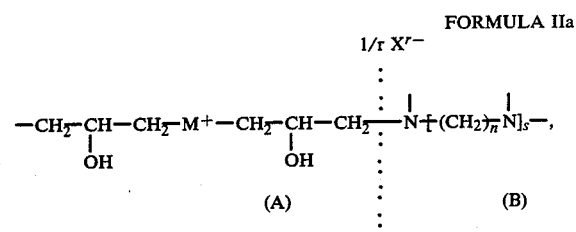    FORMULA IIa wherein r is an integer of 1–3 and represents the valence of anion X; n is an integer from 2–10; X is an anionic residue of a strong inorganic of organic acid; s is an integer of 1–4; and M is the bifunctional heterocyclic imidazole residue

This formula may be expressed in complex series as

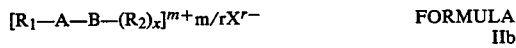    FORMULA IIb wherein r, X, n, s, and M, are as defined in Formula IIa; x is an integer of 1 or 2; A is defined as

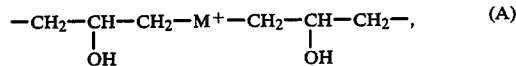    (A)

as shown in Formula IIa; and B is defined as $-[N-R_3-(CH_2)_n]_s-NR_4-$ or $-[NR_4-(CH_2)_n]_s-NR_3-$ when x=1; or as $=[N-(CH_2)_n]_s-NR_4-$; $-[N-$ $R_3$—$(CH_2)_n]_s$—N≡; ≡[N—$(CH_2)_n$—$NR_3]_s$— or —[N-$R_4$—$(CH_2)_n$—N]$_s$≡ when x=2; and wherein $R_1$ is a Cl—, —OH, or H—B— group; $R_2$ is a hydrogen, an —A—OH, —A—Cl, —A—B—H, or —A—B—A—$R_1$ group; $R_3$ and $R_4$ are each selected from the group consisting of a hydrogen or an alkyl group having 1-4 carbon atoms; and m is an integer from 1-5 and represents the number of A groups in the molecule.

The structural group of Formula II is prepared by reaction of (a) a compound of Formula I, [Y—M—Y]$^+$1/rX$^{r-}$, wherein r and X are as defined above and Y is

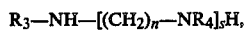

with (b) a polyfunctional amine of the formula $R_3$—NH—$[(CH_2)_n$—$NR_4]_s$H,     FORMULA IIIa wherein n is an integer of 2-10; s is an integer of 1-4; and R is a hydrogen atom or an alkyl group with 1-4 carbon atoms. The molar ratio of a compound of Formula I to Formula III is from 0.5 to 10, and the reaction takes place at a temperature of from 10° to 100° C. This formula may be abbreviated as

     FORMULA IIIb, according to the definitions, given above.

Each mole of the compound of Formula I is reacted with from 0.1 to 2 moles of the compound of Formula III. The preferred ratio ranges from 1:0.5 to 1:1. Polyfunctional amines of FORMULA III can be synthesized from substances known in epoxy resin chemistry, such as ethylene diamene, diethylene triamine, and triethylene tetramine.

The compounds of Formula I may be synthesized according to Dvorsky et al., U.S. Pat. No. 4,499,282. A heterocyclic compound with two nitrogen atoms is quaternized by epichlohydrin using an aqueous salt solution of a strong acid in a ratio of one mole of salt to 2 moles epichlorhydrin. After quaternization, the polyfunctional amines of Formula III or an aqueous solution thereof, according to the invention, are gradually added to the final reaction mixture containing the compounds of Formula I. An exothermic reaction occurs, creating the inventive complex of Formula II. The reaction occurs at a temperature of from 10° to 100° C., preferably 40° to 60° C. The final product can be used without further processing.

Three substituents may complete valence of the terminal carbon. When the quaternary ammonium precursor of Formula I is synthesized with a Y group containing chlorine, the end group is chlorine (—Cl). When a Y group without chlorine is used, the compound terminates with a hydroxyl group (—OH). In addition, there may be cross-linking between the terminal carbon of one molecule of Formula II and a nitrogen atom of another. Four substituents may complete the valences of the two nitrogen atoms shown in Formula II. The simplest of these are a hydrogen atom, or an acyl group with 1-3 carbon atoms. The inventive compound may also terminate at one or more of its nitrogens in a polyelectrolyte of Formula I, or it may bind to the terminal carbon atom of another companion molecule. Various terminal substituents are illustrated by the following composite figure, Formula IV, with reference to the Formulas IIa and IIb, and the alternative groups B defined therein.

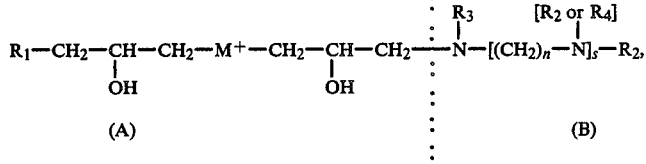

FORMULA IV.

Formula IV can be abbreviated as $[R_1$—A—B—$(R_2)_x]^+$1/rX$^{r-}$     FORMULA V.

Formula IIb can be readily derived from Formula V. When m=1 to 3 (for x=1) or m=1 to 5 (for x=2), Formula IV becomes $R_1$—A—B—$(R_2)_x]^{m+}$m/rX$^{r-}$     FORMULA IIb.

All of the substituents are as defined above.

The compounds of the invention are best used in aqueous solution ranging from 40-60%. Higher concentrations are too viscous, while lower concentrations decrease efficiency. To achieve this concentration, compounds of Formula I are prepared in aqueous solution having a concentration within the range of 70-85%; while the polyfunctional amines are prepared in aqueous solution having a concentration within the range of 40-50%. At concentrations of 40-60%, the inventive compounds of Formula II are yellow-brown viscous liquors miscible with water and having a specific weight of 1.3 1.5 g/cm$^3$.

Table 1 sets forth the precursors (Formulas I and III) for six of the inventive compound of Formula II. Table 2 sets forth the structural formula for six embodiments of the invention.

The present compounds are useful in textile finishing technology. In alkaline media, a portion of each complex compound of Formula II reacts with alcohol (—OH) groups in the cellulose macromolecule and causes additional and improved cross-linking by binding the groups containing quaternary nitrogen atoms. The result is a substantial improvement in anionic and direct dye processes. The cation-active polyelectrolytes interact with direct dyes in a manner similar to that of known fixing agents, such as those derived from dicyandiamide, but without loss of fastness due to light.

Removal of hydrolyzed independent anionic dye from cellulose takes place as follows: Cation-active polyelectrolytes, dissolved in a bath, react with independent anionic dye and form an unaffined set. The anionic dye is entrained due to the influence of the opposite charge of the anionic dye and the cation-active polyelectrolyte. The unaffined set forms relatively small elements which are at the limit of solubility. The unaffined set possesses no bonding forces with respect to the cellulose substrate, and it is therefore easily removed by rinsing. Only anionic dye bonded covalently remains on the cellulose substrate. Accordingly, blocking of independent anionic dye does not occur, which would otherwise be the case with quaternary ammonium compounds used for improving dye fastness by subsequent treatment in a bath containing quaternary ammonium compounds. The present method, which employs cation-active polyelectrolytes, exhibits higher dye fastness values and superior washing-out effects.

A particular improvement is achieved with respect to finishing processes following treatment with reactive dyes. Further, the polyelectrolyte portion of the inventive compound forms a complex with the excess dye molecules and unabsorbed portions thereof; and this complex has no affinity for cellulose fibers. As a result, treatment with the inventive compounds according to the method herein prevents any further reaction between the cellulose fibers and the excess dye. In this manner, bleeding is prevented, and improved color fastness is achieved. The invention may also be used to repair textiles damaged by bleeding from nonfixed reactive dyes.

The finishing process of the invention is characterized by an intense washing effect which functions without any alteration of existing machinery, and without any loss of print fastness from exposure to light. In addition, the use of cation-active polyelectrolytes shortens the washing process, thereby reducing water, energy, and labor expenditures.

Depending on the finishing machinery, the amount of cation-active polyelectrolyte used, in an aqueous bath, is from 0.1 to 20 g/l. Textile fabrics are washed in this bath at temperatures of 15°–100° C. for from 10 seconds to one hour. The washing effect increases with temperature: the preferred range is 80°–100° C.

The arrangement of —NH— and —OH groups achieved by the invention permits the cationic polyelectrolytes to bind metallic cations and further stabilize the dye with regard to wet and light fastness. The dye can be treated with an aqueous salt of a suitable metal, such as water soluble salts of $Ca^{2+}$; $Mg^{2+}$; $Zn^{2+}$; $Cu^{2+}$; $Fe^{2+}$; $Fe^{2+}$; $Co^{2+}$; and $Ni^{2+}$. An aqueous salt containing from 0.1 to 20 g/l of a bivalent or trivalent cation may be used, and the fabric may be treated with this solution during or after treatment with the cation-active polyelectrolyte.

The invention is further described by a number of examples, which are presented for purposes of illustration only. It will be appreciated by those skilled in the art that these examples do not serve to limit the scope of the disclosure or the appended claims.

EXAMPLE 1

An 83% aqueous solution of 1,3-bis(3-chloro-2-hydroxypropyl)imidiazoliniumsulphate (318 g) was added to a four-neck glass flask provided with a reflux condenser, a stirrer, a thermometer and a dosage separatory funnel. The temperature was adjusted to 25° C., and 120 g of 50% ethylenediamide was added to the flask under steady agitation over a 60 minute period. The temperature of the reaction mixture began to rise spontaneously. By means of cooling with continued introduction of ethylenediamide, the temperature was held within the range of 65° to 70° C. After dosing the total amount of ethylenediamide the mixture was allowed to react for another 30 minutes. Then, after cooling, the reaction mixture was a yellow-brown liquid with specific weight of 1.43 g/cm$^3$, which was miscible with water in any ratio.

EXAMPLE 2

An aqueous solution of 83% 1,3-bis(3-chloro-2-hydroxypropyl)imidazoliniumsulphate containing (140 kg) was added to an enamelled duplicator provided with a stirrer, theremometer and reflux condenser. At a temperature of 25° C., a 50% aqueous solution of diethylenetriamine (80 kg) was added gradually, so that the temperature of the reaction mixture did not exceed 70° C.

After adding the full dose diethylenetriamine, the mixture was allowed to react at 70° C. for another 45 minutes, whereupon it was cooled. The reaction produced a viscous brown liquor with a specific weight of 1.47 g/cm$^3$.

Additional compounds of the invention can be prepared by using, in place of diethylenetriamine:
50% hexamethylene diamine (110 kg)
50% N,N'-dimethylethylene diamine (70 kg)
50% triethylene tetramine (116 kg)

EXAMPLE 3

Mercerized cotton yarn dyed to a 2% depth by Direct Orange C.I. 30 was treated for 10 minutes at 30° C. in a bath containing 1 g/l of the compound of Example 1, at a liquor ration of 1:20. This process was followed by centrifuging and drying. The treated yarn exhibited very good water, sweat, and wash (40° C.) fastness values.

EXAMPLE 4

The cotton yarn of Example 3 was treated for 30 minutes in a 50° C. bath containing 5 g/l of the compound of Example 1, and 2 g/l of sodium hydroxide. The liquor ratio was 1:20. After washing and neutralizing, the yarn was dyed. The yarn exhibited excellent water, sweat, and wash (95° C.) fastness values exceeding the fastness level of Example 3.

EXAMPLE 5

Cotton fabric was pretreated on a dyeing winch by a conventional scouring and bleaching process. The fabric was then treated for 50 minutes in a 55° C. bath containing 15 g/l of compound No. 2 of Table 1 and 6 g/l sodium hydroxide, with a liquor ratio of 1:20.

After washing, the fabric was dyed with Reactive Blue C.I.4. This achieved double the effective yield of the dye by comparison with conventional processes.

EXAMPLE 6

A woven fabric made of a mixture of polyester and cellulose fibers (67–33%) was impregnated in a padder by a bath containing 10 g/l Disperse Blue C.I. 73; 3 g/l Reactive Blue C.I. 5; and 2 g/l sodium alginate.

The fabric was dried at 100° C. and was treated by a thermosol process at 195° C. within a 50 second period. The fabric was then impregnated by a bath containing 60 g/l of compound 1 from Table 1, and 20 g/l of sodium hydroxide.

After passing through the padder, with squeezing to 70%, the fabric was allowed to mature for 10 hours under rotation at room temperature. During maturation a thorough fixation of reactive dye and cross-linking of cellulose fibers by the compound of the invention took place, whereby an improved non-iron finish was obtained.

EXAMPLE 7

A cotton fabric was printed by six printing units containing Reactive Yellow C.I. 3; Reactive orange C.I. 5; Reactive Red C.I. 24; Reactive Blue C.I. 5; Reactive Green C.I. 8; and Reactive Black C.I. 8.

The fabric was also treated with a thickener, alkali, and an anti-reducing agent. After steam fixation, the fabric was washed in an open-width washing maching having eight sections containing the respective baths: cold water; 50° C. water; 3 baths of 2 g/l cation-active polyelectrolyte No. 1 from Table 1 at 90° C.; 80° C. water; 50° C. water; and cold water.

By a single passage of the fabric through the washing machine at the speed of 70 m/min, a perfect washing-out of the nonfixed dye was achieved, and the print exhibited high water and wash fastness value. The light fastness was not influenced.

EXAMPLE 8

Cotton yarn wound on X-spools was conventionally dyed in a dyeing apparatus with Reactive Orange C.I. 4 (2%); Reactive Red C.I. 2 (3.5%); and Reactive Blue C.I. 4 (0.2%).

The dyed yarn was washed in cold water for 5 minutes, and for another 5 minutes in water at 50° C. Then the yarn was treated by an aqueous 90° C. bath containing 2 g/l of cation-active polyelectrolyte No. 1 from Table 1 for a period of 10 minutes. This process was and by a short rinse in cold water. The fastness values of this very deep dyeing were 4-5 4-5 4-5, whereas the dyeing finished by a conventional method exhibited water fastness values of 4 3 4.

EXAMPLE 9

A knitted fabric made from a mixture of cotton and rayon staple fiber was dyed conventionally in a hydro-dynamic dyeing maching by 4.5% reactive red C.I. 2. After dyeing, the fabric was washed for 5 minutes in water at 20°-25° C.; for another 5 minutes in water at 60° C., and subsequently at 90° C. for 10 minutes in an aqueous bath containing 2 g/l of cation-active polyelectrolyte No. 3 from Table 1.

The wet fastness values exceeded those achieved by conventional finishing processes.

EXAMPLE 10

A cotton woven fabric dyed in a jigger by Direct Blue C.I. 78 (2% depth) was subsequently washed by cold water and treated at 30° C. in a bath containing 5 g/l of compound No. 1 from Table 1 in a 1:5 liquor ratio. The fixed dye exhibited excellent water fastness and good wash fastness values.

EXAMPLE 11

A cotton woven fabric dyed and fixed according to Example 3 was subsequently treated at 60° C. for 20 minutes in a bath containing 2.5 g/l of crystalline copper (II) sulphate; and 1.0 ml/l of glacial acetic acid in a 1:5 liquor ratio. In this way the wash and light fastness values were further increased.

TABLE 1

| COMPOUND NUMBER | BASIC SUBSTANCES | | | |
|---|---|---|---|---|
| | $[Y-M-Y]^+$ $1/r$ $X^{r-}$ | | $R_3-NH-[(CH_2)_n-NR_4]_xH$ | |
| 1 | 1,3-bis(3-chloro-2-hydroxypropyl) imidizolinium sulphate | 1 mole | ethylenediamine | 1 mole |
| 2 | 1,3-bis(3-chloro-2-hydroxypropyl) imidizolinium sulphate | 1 mole | diethylene triamine | 0.8 mole |
| 3 | 1,3-bis(2,3-epoxypropyl) imidizolinium chloride | 1 mole | triethylene tetramine | 0.6 mole |
| 4 | 1,3-bis(3-chloro-2-hydroxypropyl) imidizolinium acetate | 1 mole | hexamethylene diamine | 1 mole |
| 5 | 1,3-bis(3-chloro-2-hydroxypropyl) imidizolinium acetate | 1 mole | N,N'—dimethylhexamethylene diamine | 1 mole |
| 6 | 1,3-bis(3-chloro-2-hydroxypropyl) imidizolinium acetate | 1 mole | ethylenediamine | 0.8 mole | followed by washing with 50° C. water for 5 minutes

TABLE 2

| COMPOUND NUMBER | Basic structural unit |
|---|---|
| 1 | $-CH_2-CH(OH)-CH_2-N^{\oplus}\smile N-CH_2-CH(OH)-CH_2-N-CH_2-CH_2-N-$ ; $\tfrac{1}{2}SO_4^{2-}$ |
| 2 | $-CH_2-CH(OH)-CH_2-N^{\oplus}\smile N-CH_2-CH(OH)-CH_2-N-CH_2-CH_2-N-CH_2-CH_2-N-$ ; $Cl^-$ |
| 3 | $-CH_2-CH(OH)-CH_2-N^{\oplus}\smile N-CH_2-CH(OH)-CH_2-N-CH_2-CH_2-N-CH_2-CH_2-N-CH_2-CH_2-N-$ ; $Cl^-$ |

TABLE 2-continued

| COMPOUND NUMBER | Basic structural unit |
|---|---|
| 4 | $-CH_2-CH(OH)-CH_2-N^{\oplus}\diagdown N-CH_2-CH(OH)-CH_2-N-(CH_2)_6-N-$ ; $\frac{1}{2}SO_4^{2-}$ |
| 5 | $-CH_2-CH(OH)-CH_2-N^{\oplus}\diagdown N-CH_2-CH(OH)-CH_2-N(CH_3)-(CH_2)_6-N(CH_3)-$ ; $CH_3COO^-$ |

We claim:

1. A water-soluble cation-active polyelectrolyte of the formula $$[R_1-A-B-(-R_2)_x]^{m+}m/rX^{r-}$$

wherein,
r is an integer of 1–3,
m is an integer of 1–5,
x is an integer of 1 or 2,
X is selected from an anionic residue of a strong inorganic acid and a strong organic acid,
A is defined as $-CH_2-CHOH-CH_2-M^+-CH_2-CHOH-CH_2-$,
M is a heterocyclic imidazole residue,
B is selected from the group consisting of $-[N-R_3-(CH_2)_n]_s-NR_4-$ and $-[NR_4-(CH_2)_n-]_s-NR_3-$ when $x=1$ and $=[N-(CH_2)_n-]_s-NR_4-$, $-[NR_3-(CH_2)_n]_s-N=$, $=[N-(CH_2)_n-NR_3]_s-$, and $-[NR_4-(CH_2)_n-N]_s=$, when $x=2$,
$R_1$ is selected from the group consisting of $Cl^-$, $-OH$, and $H-B-$,
$R_2$ is selected from the group consisting of a hydrogen, $-A-OH$, $-A-Cl$, $-A-B-H$, and $-A-B-A-R_1$,
$R_3$ and $R_4$ are each selected from the group consisting of a hydrogen and an alkyl group having 1 to 4 carbon atoms,
n is an integer of from 2 to 10, and
s is an integer of from 1 to 4.

2. A cation-active polyelectrolyte of the formula $$[R_1-A-B-(R_2)_x]^{m+}m/rX^{r-},$$

wherein
A is $-CH_2-CH(OH)-CH_2-M^+-CH_2-CH(OH)-CH_2-$,
M is a bifunctional heterocyclic imidazole residue,
B is selected from the group consisting of $-[N-R_3-(CH_2)_n]_s-NR_4-$ and $-[NR_4-(CH_2)_n-]_s-NR_3-$ when $x=1$ and $=[N-(CH_2)_n-]_s-NR_4-$, $-[NR_3-(CH_2)_n]_s-N=$, $=[N-(CH_2)_n-NR_3]_s-$, and $-[NR_4-(CH_2)_n-N]_s=$, when $x=2$,
$R_1$ is selected from the group consisting of $Cl^-$, $-OH$, and $H-B-$,
$R_2$ is selected from the group consisting of H, $-A-Cl$, $-A-OH$, $-A-B-H$, and $-A-B-A-R_1$,
$R_3$ and $R_4$ are each selected from the group consisting of a hydrogen and an alkyl group having 1 to 4 carbon atoms,
x is an integer of 1 or 2,
n is an integer from 2 to 10,
s is an integer from 1 to 4,
X is an anion of a strong organic or inorganic acid,
r is a valence of anion X and ranges from 1 to 3, and
m is the number of A groups, ranging from 1 to 5.

* * * * *